(12) United States Patent
Raza et al.

(10) Patent No.: US 6,858,618 B2
(45) Date of Patent: Feb. 22, 2005

(54) USE OF ROSUVASTATIN (ZD-4522) IN THE TREATMENT OF HETEROZYGOUS FAMILIAL HYPERCHOLESTEROLEMIA

(75) Inventors: Ali Raza, Cheshire (GB); Howard Gerard Hutchinson, Delaware, DE (US)

(73) Assignee: AstraZeneca AB, Sodertalje (SE)

( * ) Notice: Subject to any disclaimer, the term of this patent is extended or adjusted under 35 U.S.C. 154(b) by 31 days.

(21) Appl. No.: 10/432,402

(22) PCT Filed: Nov. 16, 2001

(86) PCT No.: PCT/GB01/05041
§ 371 (c)(1),
(2), (4) Date: Nov. 6, 2003

(87) PCT Pub. No.: WO02/41895
PCT Pub. Date: May 30, 2002

(65) Prior Publication Data
US 2004/0072852 A1 Apr. 15, 2004

(30) Foreign Application Priority Data
Nov. 22, 2000 (GB) .............................................. 0028429

(51) Int. Cl.$^7$ ............................................. A61K 31/505
(52) U.S. Cl. ....................................................... 514/275
(58) Field of Search ........................................ 514/275

(56) References Cited
U.S. PATENT DOCUMENTS 6,316,460 B1 * 11/2001 Creekmore et al. .......... 514/275
6,696,084 B2 * 2/2004 Pace et al. ................... 424/451

FOREIGN PATENT DOCUMENTS
EP        0 521 471 A     1/1993

OTHER PUBLICATIONS

Koizumi et al., "Clinical Efficacy of Fluvastatin in the Long–Term Treatment of Familial Hypercholesterolemia", American Journal of Cardiology, vol. 76, No. 2, 1995, pp. 47A–50A.

Kitatani et al., "A 4–Year trial of simvastatin in the treatment of patients with heterozigous of Familial Hypercholesterolaemia", Current Therapeutic Research, vol. 57, No. 1, 1996, pp. 62–71.

Koizumi et al., "Reduction of lipoprotein (a) by LDL–apheresis using a dextran sulfate cellulose column in patients with familial hypercholesterolemia", Atherosclerosis, vol. 100, No. 1, 1993, pp. 65–74.

Stein et al., "Efficacy and safety of lovastatin in adolescent males with heterozygous familial hypercholesterolemia: A randomized controlled trial", Journal of American Medical Association, vol. 281, No. 2, Jan. 13, 1999, pp. 137–144.

Watanabe et al., "Synthesis and Biological Antivity of Methanesulfonamide Pyrimidine–And–N–Methanesulfonyl Pyrrole–Substituted 3,5–Dihydroxy–6–Heptenoates, A Novel Series of HMG–COA Reductase Inhibitors", Bioorganic & Medicinal Chemistry, Elsevier Science Ltd., vol. 5, No. 2, 1997, pp. 437–444.

Olsson et al., "ZD4522: A new HMG–CoA reductase inhibitor–causes rapid and profound reductions in plasma LDL–C levels in patients with primary hypercholesterolaemia", European Heart Journal, vol. 21, no. Abstract Supplement, Aug., 2000, p. 156.

Pears et al., "Dose–ranging study of the HMG–CoA reductase inhibitor ZD4522 in patients with primary hypercolesterolemia", Canadian Journal of Cardiology, vol. 16, No. Supplement F, Sep. 2000, p. 196F.

Stein et al., "ZD4522 (rosuvastatin) compared with diet and maximal lipid therapy in patients with heterozygous familial hypercholesterolemia", Journa of the American College of Cardiology, vol. 37, No. 2, Supplement A, Feb. 2001, p. 291A.

Stein et al., "ZD4522 is superior to atorvastatin in the treatment of patients with heterozygous familial hypercholesterolemia", Journal of American College of Cardiology, vol. 37, No. 2, Supplement A, Feb. 2001, p. 292A.

Ollson et al., "A new statin: A new Standard", Clinical Cardiology, vol. 24, No. 8, Supplement 3, Aug. 2001, pp. III–18–III–23.

* cited by examiner

Primary Examiner—Raymond J. Henley, III
(74) Attorney, Agent, or Firm—Morgan Lewis & Bockius LLP

(57) ABSTRACT

The invention provides a method for the treatment of heterozygous familial hypercholesterolemia by administering the compound (E)-7-[4-(4-fluorophenyl)-6-isopropyl-2-[methyl(methylsulfonyl)amino]pyrimidin-5-yl](3R,5S)-3,5-dihydroxyhept-6-enoic acid or a pharmaceutically acceptable salt thereof.

10 Claims, 1 Drawing Sheet

ZD4522

USE OF ROSUVASTATIN (ZD-4522) IN THE TREATMENT OF HETEROZYGOUS FAMILIAL HYPERCHOLESTEROLEMIA

This application is a 371 of PCT/GB01/05041 filed Nov. 16, 2001.

The present invention relates to a new use of a statin drug in the treatment of severe heterozygous familial hypercholesterolemia (HeFH) and in particular patients with baseline LDL-C>220 mg/dL There is now a large body of evidence obtained from clinical trials demonstrating that pharmacological agents (particularly the statins) that reduce low density lipoprotein-cholesterol LDL-C levels also decrease Chronic Heart Disease (CHD) risk (Lipid Research Clinics Program 1984, Gould et al 1998). Taken together, the trials published to date support the concept that lowering LDL-C levels should be the principal goal of lipid altering therapy (Ansell et al 1999), and that the reduction in coronary risk that occurs during treatment with statins is directly related to these agents' LDL)C lowering effects (Gould et al 1998, Pedersen et al 1998).

Primary hyperlipidemia is a term used to describe a defect in lipoprotein metabolism. The lipoproteins commonly affected are LDL-C, which transports mainly cholesterol, and VLDL-C, which transports mainly TG. Most subjects with hyperlipidemia have a defect in LDL metabolism, characterised by raised cholesterol, LDL-C, levels, with or without raised triglyceride levels; such subjects are termed hypercholesterolemic (Fredrickson Type II). Familial hypercholesterolemia (FH) is caused by any one of a number of genetically-determined defects in the LDL receptor, which is important for the entry of cholesterol into cells. The condition is characterised by a reduced number of functional LDL receptors, and is therefore associated with raised serum LDL-C levels due to an increase in LDL In its heterozygous form (HeFH) it is one of the commonest genetic diseases, with a frequency of about 1 in 500 in the United Kingdom (US), the United States (US), and Japan (Myant 1981, Mabuchi et al 1979).

LDL and VLDL are known to be atherogenic, and thus subjects with hypercholesterolemia are at increased risk of developing atherosclerosis, a disease process that results in widespread clinical manifestations, including coronary heart disease (CHD), cerebrovascular disease (CVD) and peripheral vascular disease (PVD). In subjects with HeFH, the clinical manifestations of heart disease can occur as early as the mid-twenties. Many subjects with hypercholesterolemia die each year as a result, and many have a reduced quality of life; inevitably, this places very heavy demands on health service resources.

One important goal of therapy in these subjects is to reduce blood cholesterol levels, since this may reduce the progression of the disease and may even induce regression (Expert Panel on Detection, Evaluation and Treatment of High Blood Cholesterol in Adults 1993).

Quoting the % of subjects brought within relevant guidelines (NCEP, EAS) targets for LDL-C levels is a useful way of expressing the efficacy of lipid-regulating agents, and is becoming more commonplace in the literature. The guidelines of the National Cholesterol Education Program (NCEP) and European Atherosclerosis Society (EAS) are well recognised and have been accepted internationally.

Therapies available to treat HeFH include resins, such as cholestyramine and colestipol. Resins reduce LDL-C levels by sequestering bile acids (essential for the absorption of dietary lipid) from the gut and preventing their reabsorption; however, their use is limited by unpalatability and poor subject compliance. Fibrates, such as fenofibrate and gemfibrozil, have a complex mechanism of action on LDL-C, and appear to be of more use in reducing blood TG levels than cholesterol levels; these drugs are therefore less useful in subjects with HeFH (who typically do not have significantly elevated triglyceride levels). Fibrate drugs are thought to act through peroxisomal proliferating activator receptor-α (PPAR-α) and affect gene activation at a number of genes involved in atheroma Patients on fibrate drugs show improved LDL subfraction distribution (reduced VLDL and raised HDL), reduced LDL and reduced triglyceride levels and possible advantages through improving insulin sensitivity. Examples of fibrate drugs include, bezafibrate, ciprofibrate, fenofibrate and gemfibrozol. Nicotinic acid and its derivatives have some benefit, but are limited by prostaglandin-mediated side effects, such as flushing and dizziness.

A breakthrough in treating hypercholesterolemia has come from agents known as statins. These drugs, which include atorvastatin, pravastatin and simvastatin, lower LDL-C levels by inhibiting 3-hydroxy-3-methylglutsryl coenzyme A (HMG-CoA) reductase, the enzyme involved in the rate-limiting step in cholesterol biosynthesis in the liver. Partial inhibition of hepatic cholesterol metabolism is thought to result in an increase in the number of cellular receptors for LDL-C, leading to an increased removal of LDL-C from the circulation.

Despite the benefits of statin therapy less than optimal therapeutic results are achieved by the use of statins in patients suffering from HeFH. Typically the majority of patients suffering from HeFH are treated with at least a statin and a fibrate or a statin and a bile acid sequestrant or possibly all these in an aggressive attempt to reduce the patients LDL-C levels within acceptable guideline limits. Myopathy and rhabdomyolysis have been associated with taking a statin in combination with gemfibrozil and niacin (HMG CoA reductase inhibitors, Hunninghake, Current Opinion in Lipidology (19921) 3, 22–28) as they are all substrates for P450 3A4 and may lead to clinicalily significant drug interactions.

Therefore, currently there is no single drug treatment which may be used on its own which consistently brings a significant number of patients suffering from HeFH within NCEP or EAS guidelines Risk categories and target LDL-C levels in the NCEP and EAS guidelines

| Guideline and risk category | Definition of risk | Target LDL-C level |
| --- | --- | --- |
| NCEP | | |
| Low-risk | No CHD or PVD and ≦1 risk factor | <4.14 mmol/L (<160 mg/dl) |
| Medium risk | No CHD or PVD and ≧2 risk factors | <3.36 mmol/L (<130 mg/dL) |
| High-risk | Clinically evident CHD, PVD or diabetes | ≦2.59 mmol/L (≦100 mg/dL) |
| EAS | | |
| High-risk | CHD, diabetes or a family history of premature CHD or PVD; or assigned based on a logistic regression model | <3.00 mmol/L (<116 mg/dL) |
| Other risk | Assigned based on a logistic regression model | <3.00 mmol/L (<116 mg/dL) |

We have discovered that (E)-7-[4-(4-fluorophenyl)-6-isopropyl-2-[methyl(methylsulfonyl)amino]pyrimidin-5-yl] (3R,5S)-3,5-dihydroxyhept-6-enoic acid or a pharmaceutically acceptable salt thereof (hereinafter called ZD4522), the calcium salt of which is shown in FIG. 1 below, is particularly good at treating heterozygous familial hypercholesterolemia, in particular severe heterozygous familial hypercholesterolemia (HeFH).

Figure 1:
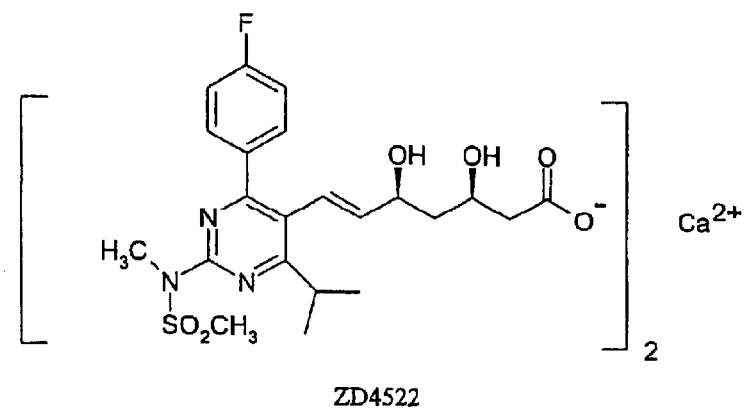
FIG. 1 shows the chemical structure of the calcium salt of Rosuvastatin.

We have conducted a Phase III trial designed to assess the efficacy of ZD4522 in subjects with HeFH. The dose-response of ZD4522 was compared with atorvastatin using the percentage change from baseline in LDL-C levels as the primary end-point. Doses of ZD4522 up to 80 mg per day were use& Atorvastatin was chosen as the comparator statin in this trial because it has the best LDL-C lowering activity of the currently marketed statins.

A larger percentage of patients with heterozygous familial hypercholesterolemia are brought within NCEP or EAS guidelines with treatment of ZD4522 alone than with any other therapy, in particular in high risk patients.

ZD4522 is a statin that demonstrates potent in vitro and in vivo inhibition of HMG-CoA reductase. Early clinical trials have shown that ZD4522 has a beneficial effect on the lipid profile, by reducing LDL-C, total cholesterol (TC) and TG levels. In addition, ZD4522 has been shown to raise high-density lipoprotein cholesterol (HDL-C) levels.

By the use of the term heterozygous familial hypercholesterolemia we mean patients who have been diagnosed with this type of condition such as patients whose genotype has been determined to be indicative of HeFH. Particular HeFH patients who benefit from ZD4522 are those suffering from severe HeFH. By the use of the term "severe HeFH" we mean patients who are high risk category patients, as defined by the NCEP guidelines (as outlined in JAMA 1993; 269:3015–23 which guidelines and charts are incorporated herein by reference), such patients target LDL-C levels being lower, i.e. $\leq 100$ mg/dL.

For the purposes of clarity patients who suffer from homozygous familial hypercholesterolemia are excluded from the scope of this invention.

Therefore we present as a first feature of the invention a method for treating heterozygous familial hypercholesterolemia in a patient suffering heterozygous familial hypercholesterolemia, comprising administering to the patient ZD4522.

ZD4522 is disclosed in European Patent Application, Publication No. 0521471, and in Bioorganic and medicinal Chemistry, (1997), 5(2), 437–444 as an inhibitor of 3-hydroxy-3-methylglutary CoA reductase (HMG-CoA reductase). Preferably the calcium salt is used as illustrated in FIG. 1. Preferably the ZD4522 is used at a dose of 5 to 80 mg per day, in particular 40 to 80 mg per day.

The pharmaceutical compositions of the present invention may be administered in a standard manner for example by oral or parenteral administration, using conventional systemic dosage forms, such as a tablets, capsules, pills, powders, aqueous or oily solutions or suspensions, emulsions, sterile injectable aqueous or oily solutions or suspensions. These dosage forms will include the necessary carrier material, excipient, lubricant, buffer, bulking agent, anti-oxidant, dispersant or the like. In particular, compositions for oral administration are preferred, for example as disclosed in International Patent Application, Publication No. WO 01/54668.

The dose of ZD4522 which can be administered in accordance with the present: invention depends on several factors, for example the age, weight and the severity of the condition under treatment, as well as the route of administration, dosage form and regimen and the desired result In the treatment of severe heterozygous familial hypercholesterolemia the maximum lipid lowering effect is desired and therefore a maximum dose of at least 40 mg a day is recommended, preferably 80 mg a day.

A unit dosage formulation such as a tablet or capsule will usually contain, for example, from 1 mg to 100 mg of ZD4522. Preferably a unit dose formulation will contain 5 to 80 mg ZD4522.

A clinical protocol testing the effectiveness of ZD4522 in heterozygous familial hypercholesterolemia and results is set out below A 24-Week, Randomised, Double-blind, Multicentre, Multinational Trial to Evaluate the Efficacy and Safety of ZD4522 and Atorvastatin in the Treatment of Subjects with Heterozygous Familial Hypercholesterolemia Objectives The primary objective was to compare the efficacy of ZD4522 (titrated to 80 mg) with that of atorvastatin (titrated to 80 mg) in reducing low-density lipoprotein cholesterol (LDL-C) levels in subjects with heterozygous familial hypercholesterolemia (HeFH) after 18 weeks of treatment.

The secondary objectives were to compare the efficacy of ZD4522 with that of atorvastatin in relation to the following: reducing LDL-C levels after 2, 6, and 12 weeks of treatment; in modifying other lipids and lipoprotein fractions after 2, 6, 12, and 18 weeks of treatment; in reducing LDL-C levels to within relevant national and international guidelines after 6, 12, and 18 weeks of treatment; in modifying the inflammatory marker C-reactive protein (CRP) after 18 weeks of treatment. A further secondary objective was to determine the safety of ZD4522.

Methods

Design: A 24-week, randomised, double-blind, 2-group, parallel-group, forced-titration, multicentre, multinational trial. After a 6-week dietary lead-in period, subjects were randomised to treatment with either ZD4522 20 mg, or atorvastatin 20 mg for 6 weeks. Following this initial treatment period, all subjects with an LDL-C level >1.3 mmol/L (50 mg/dL) were force-titrated at 6-week intervals as follows; from ZD4522 20 to 40 to 80 mg, and from atorvastatin 20 to 40 to 80 mg. The maximum titrated dose of either treatment after 18 weeks was 80 mg.

Population: A total of 265 (200 in the ZD4522 group, 65 in the atorvastatin group) randomised to and evaluable subjects with documented heterozygous F, derived from approximately 1240 recruited subjects, were required to enable 80% power in detecting a 6% difference between groups in the percentage change from baseline in LDL-C levels.

Key inclusion criteria: Men or women aged $\geq 18$ years with heterozygous FH; discontinuation of all cholesterol-lowering drugs and dietary supplements; fasting LDL-C levels between 5.69 and <12.93 mmol/L (220 and <500 mg/Ld); fasting triglyceride (TG) levels $\leq 4.52$ mmol/L (400 mg/dL); an Eating Pattern Assessment Tool (EPAT) score of $\leq 28$ to demonstrate dietary compliance.

Key exclusion criteria: Various concomitant illnesses, including active liver disease or hepatic dysfunction (defined by an alanine aminotransferase [ALT], aspartate amninotransferase [AST] or bilirubin concentration $\geq 21.5 \times$ the upper limit of normal [ULN]), active arterial disease, history of malignancy (unless basal or squamous cell skin carcinoma), uncontrolled hypertension, and uncontrolled hypothyroidism; serum creatine kinase (CK) concentration >3×ULN; usage of concomitant medications known to affect the lipid profile or present a potential safety concern (for example, through drug interaction).

Dosage: Subjects took oral doses of trial treatment once daily, approximately 3 hours after the evening meal. Doses of treatments were as follows; ZD4522 20, 40, and 80 mg, atorvastatin 20, 40, and 80 mg. Subjects had their doses titrated up at 6-week intervals in a sequential manner, if appropriate.

Key assessments:

Efficacy: Fasting LDL-C, total cholesterol (TC), high-density lipoprotein cholesterol (HDL-C), and TG were assessed at, Weeks 0, 2, 6, 12, and 18; fasting apolipoprotein (ApoB) and apolipoprotein A-I (ApoA-I) were assessed at Weeks 0 and 18; C-reactive protein (CRP) was assessed at Weeks 0 and 18. Dietary compliance throughout the trial was assessed and evaluated.

The primary end-point was the percentage change from baseline to Week 18 in LDL-C levels, and was analysed using analysis of variance (ANOVA) on last observations carried forward (LOCF) from an intention-to-treat (ITT) population; the initial ANOVA model included terms for treatment, center, and center-by-treatment interaction. Additional analyses using observed data from ITT and per-protocol (PP) populations were used to confirm the robustness of the Main ITT analysis.

Percentage changes from baseline in the other lipids and lipoproteins were secondary end-points of the trial and were analysed using ANOVA. The other secondary end-points of the percentage of subjects in the ITT population who achieved targets for LDL-C levels specified by the National Cholesterol Education Program (NCEP) or the European Atherosclerosis Society (EAS), and the percentage change from baseline in the inflammatory marker CRP, were summarised only.

Subgroup and exploratory analyses were performed on LDL-C and HDL-C data, based on predefined demographic groupings.

Safety: Standard safety assessments included adverse event pot clinical laboratory data (hepatic biochemistry, CK, renal biochemistry, haematology, urinalysis), vital signs, electrocardiograms (ECGs) and physical examination.

Results

Demography: A total of 999 subjects were recruited from 58 centres, and of these, 623 subjects from 57 centres (the one subject in Center 0254 was not randomised) were eligible for randomisation after the dietary lead-in period. A total of 435 subjects were given ZD4522 20/40/80 mg and 187 subjects were given atorvastatin 20/40/80 mg; one subject who was randomised to the ZD4522 20/40/80 mg treatment group did not take study medication and was excluded from both ITT and safety populations. Though the number of subjects recruited was lower than the projected number of 1240, the number of screen failures/withdrawals during the dietary lead-in period was approximately half the anticipated failure rate of 60%. As all subjects recruited who had satisfied randomisation criteria were allowed the opportunity to complete the trial and both treatment groups were consequently over-recruited by approximately 100 subjects each. Demographic characteristics were generally well balanced among the treatment groups. The majority of subjects were Caucasians between 18 and 65 years of age, with a mean Body Mass Index (BMI) of 27.13 kg/m2. There were 376 screen failures/withdrawals during the dietary lead-in period, of whom the majority (88%) were screen failures, defined as the failure to meet inclusion/exclusion. Of the 623 subjects randomised to treatment, 34 withdrew; adverse events were the most common reason for withdrawal (71% of subjects withdrawing during the randomisation period). There were 622 subjects in the safety population and the same 622 subjects included the ITT population; there were 514 subjects in the PP population. A total of 589 subjects successfully completed the trial.

Efficacy: A summary of the key efficacy findings is presented in Table I.

TABLE I

Summary of key efficacy findings (LOCF on ITT population)

| Efficacy end-point | ZD4522 20/40/80 mg[a] | Atorvastatin 20/40/80 mg[a] |
|---|---|---|
| Lsmean of percentage change from baseline to Week 18 in lipids and lipid ratios | | |
| LDL-C | −57.88[b] | −50.41[b] |
| TC | −46.35[b] | −42.13[b] |
| HDL-C | 12.36[b] | 2.91[b] |
| TG | −27.82[ns] | −31.60[ns] |
| LDL-C/HDL-C | −61.69[b] | −51.16[b] |
| TC/HDL-C | −51.44[b] | −43.17[b] |
| Non-HDL-C/HDL-C | −59.40[b] | −49.86[b] |
| ApoB | −50.21[b] | −44.44[b] |
| ApoA-I | 5.86[b] | −2.33[b] |
| ApoB/ApoA-I | −52.03[b] | −42.46[b] |
| Percentage subjects reaching NCEP or EAS targets for LDL-C levels at Week 18 | | |
| NCEP, overall | 60.5 | 46.0 |
| NCEP, high-risk | 23.9 | 3.2 |
| EAS, overall | 47.4 | 24.1 |
| EAS, high-risk | 47.5 | 24.2 |
| Percentage change from baseline to Week 18 in inflammatory marker (Observed data) | | |
| CRP | 25.21 | 31.28 |

[a]Although force-titrations were scheduled to take place at 6-week intervals, any subject whose most recently recorded LDL-C level was ≦1.3 mmol/L (50 mg/dl) remained on their current dose of trial medication and did not proceed with the next scheduled dose-titration step.
[b]$p < 0.001$, [ns]= not significant versus atorvastatin 20/40/80 mg ($p = 0.052$).
Statistical analysis was not performed for NCEP and EAS targets.
lsmean = Least squares mean.

In the primary efficacy analysis (LOCF data from the SIT), ZD4522 20/40/80 mg resulted in a significantly ($p<0.001$) greater % reduction in LDL-C levels than did atorvastatin 20/40/80 mg at 18 weeks. The difference between treatments was >6%, the difference on which the trial was powered, and was therefore considered to be clinically relevant (mean % reduction in LDL-C was 57.88% in the ZD4522 20/40/80 mg group and 50.41% in the atorvastatin 20/40/80 mg group). ZD4522 resulted in significantly ($p<0.001$) and clinically greater % reduction in LDL-C at Week 2, 6 and 12. ZD4522 20/40/80 mg also resulted in significantly ($p<0.001$) greater % reductions in TC and significantly ($p≦0.003$) greater % increase in HDL-C than did atorvastatin 20/40/80 mg at all time points (observed data for Week 2, 6 and 12; observed and LOCF for Week 18). Both ZD4522 20/40/80 mg and atorvastatin 20/40/80 mg reduced TG levels at all time point, but the % reductions were similar in both treatment groups and the differences were not significantly different ($p>0.050$ at 2, 6 and 12 weeks for observed data and 18 weeks for LOCF). ZD4522 20/40/80 mg resulted in significantly ($p<0.001$) greater decreases in ApoB and increases in ApoA-I than did atorvastatin 20/40/80 mg at Week 18 (LOCF). In addition, ZD4522 20/40/80 mg resulted in significantly ($p<0.001$), greater reductions in the LDL-C/HDL-C, TC/HDL-C and non-HDL-C/HDL-C ratios at all time points.

The same finding was true for the ApoB/ApoA-I ratio at Week 18 (LOCF). A greater percentage of subjects in the ZD4522 20/40/80 mg group achieved NCEP and EAS target levels than did those in the atorvastatin 20/40/80 mg group, with the greatest difference between treatments observed for the NCEP high-risk group. Analysis of % change in CRP showed no apparent treatment-related differences; however, data were extremely variable. Results from the PP population generally supported these results. Exploratory and subgroup analyses of % LDL-C reduction from baseline showed significant effects for the following variables: age, baseline HDL-C and baseline TG. Treatment effect was also a significant variable for the baseline TG.

Overall Conclusions

ZD4522 was significantly more effective than atorvastatin in improving the atherogenic lipid profile (LDL-C, HDL-C and TC); ZD4522 was also clinically superior to atorvastatin with respect to effect on LDL-C levels, the primary lipid of interest. ZD4522 resulted in more subjects achieving guideline targets for LDL-C than did atorvastatin, particularly with those at high-risk of cardiovascular disease. ZD4522 had a satisfactory safety profile, which was comparable to atorvastatin.

Primary Endpoint

The main efficacy analyses were based on the ITT (LOCF at 18 weeks); PP and 18 week observed data analyses support use of ITT LOCF analyses.

ZD4522 reduced LDL-C statistically and clinically significantly more than did atorvastatin at 18 weeks.

Secondary Endpoints

ZD4522 reduced LDL-C statistically and clinically significantly more than did atorvastatin at 2, 6 and 12 weeks.

ZD4522 reduced TC statistically significantly more than did atorvastatin at 2, 6, 12 and 18 weeks.

ZD4522 increased HDL-C statistically significantly more than did atorvastatin at 2, 6, 12 and 18 weeks.

ZD4522 and atorvastatin demonstrated similar efficacy in reducing TG at all time points.

ZD4522 reduced Apo B and increased Apo A-I statistically significantly more than did atorvastatin at 18 weeks.

ZD4522 reduced all four ratios statistically significantly more than did atorvastatin at all time points assessed (LDL-C/HDL-C, TC/HDL-C, non-LDL-C/HDL-C at 6, 12 and 18 weeks and Apo B/Apo A-I at 18, weeks).

ZD4522 brought a greater proportion of patients within NCEP and EAS guideline targets for LDL-C than did atorvastatin at all time points. This was particularly apparent in the high-risk category patients and was more marked as treatment progressed.

CRP data were highly variable and there were no apparent treatment-related differences.

The overall incidence of AEs in the two treatment groups (including treatment-related AEs, AEs leading to withdrawals and SAEs) was similar (61.8% and 65.8% for ZD4522 and atorvastatin, respectively). Overall, there were no treatment-related trends and there were no trends towards increasing incidence with increasing dose.

There were no clinically significant elevations ($\geq 10\times$ ULN) in CK on either treatment. The incidence of clinically significant elevations in ALT ($\geq 3\times$ULN) was 2.3% (10 patients) in the ZD4522 group and 1.1% (2 patients) in the atorvastatin group. The numbers of patients were too small to allow comparative inferences.

Data on vital signs, ECGs and ophthalmological assessments suggested no obvious differences between treatment groups.

Abbreviations and Conventions

| ABBREVIATIONS | |
| --- | --- |
| Abbreviation | Definition |
| ALP | Alkaline phosphatase |
| ALT | Alanine aminotransferase (also known as SGPT, serum glutamic pyruvate transaminase) |
| ANOVA | Analysis of variance |
| ApoB | Apolipoprotein B |
| ApoA-I | Apolipoprotein A-I |
| AST | Aspartate aminotransferase (also known as SGOT, serum oxaloacetic pyruvate transaminase) |
| BMI | Body mass index |
| CHD | Coronary heart disease |
| EAS | European Atherosclerosis Society |
| FH | Familial hypercholesterolaemia |
| HDL | High-density lipoprotein |
| HDL-C | High-density lipoprotein cholesterol |
| HMG-CoA | 3-Hydroxy-3-methylglutaryl coenzyme A |
| ITT | Intention-to-treat |
| LDL | Low-density lipoprotein |
| LDL-C | Low-density lipoprotein cholesterol |
| LOCF | Last observation carried forward |
| NCEP | National Cholesterol Education Program |
| PP | Per protocol |
| PVD | Peripheral vascular disease |
| TC | Total cholesterol |
| TG | Triglyceride |
| ULN | Upper limit of normal |
| VLDL | Very-low-density lipoprotein |

References

Ansell B J, Watson K E, Fogelman A M. An evidence-based assessment of the NCEP Adult Treatment Panel II Guidelines. JAMA 1999;282:2051–7.

Frick M H, Elo O, Haapa K, Heinonen O P, Heinsalmi P, Helo P et al. Helsinki Heart Study: Primary-prevention trial with gemfibrozil in middle-aged men with dyslipidemia. Safety of treatment, changes in risk factors, and incidence of coronary heart disease. N Engl J Med 1987;317:1237–45.

Gotto A M. Triglyceride as a risk factor for coronary artery disease. Am J Cardiol 1998;92:22Q–25Q.

Gould A L, Rossouw J E, Santanello N C, Heyse J F, Furberg C D. Cholesterol reduction yields clinical benefit. Impact of statin trials. Circulation 1998;97:946–52.

Mabuchi H, Tatami R, Veda K, Veda R, Haba T et al. Serum lipid and lipoprotein levels in Japanese subjects with familial hypercholesterolemia. Atherosclerosis 1979;32:435–444.

Myant N B. Disorders of cholesterol metabolism: the hyperlipoproteinaemias. In: The biology of cholesterol and related steroids. London: Heinemann Medical, 1981:689–772.

Pedersen T R, Olsson A G, Faergeman O, Kjekshus J, Wddel H, Berg K et al. Lipoprotein changes and reduction in the incidence of major coronary heart disease events in the Scandinavian Simvastatin Survival Study (4S). Circulation 1998;97:1453–60.

Rubins H B, Robins S J, Collins D, Fye C L, Anderson J W, Elam M B et al. Gemfibrozil for the secondary prevention of coronary heart disease in men with low levels of high-density lipoprotein cholesterol. N Engl J Med 1999;341:410–8.

EXAMPLE 1

| Capsule | mg |
|---|---|
| ZD4522 | 5.0 |
| Lactose | 42.5 |
| Corn starch | 20.0 |
| Microcrystalline cellulose | 32.0 |
| Pregelatinised starch | 3.3 |
| Hydrotalcite | 1.1 |
| Magnesium stearate | 1.1 |

Capsules containing 1, 2.5 or 10 mg of the ZD4522 may be obtained similarly using more or less lactose as appropriate., to achieve a fill weight of 105 mg.

EXAMPLE 2

| Tablet | mg |
|---|---|
| ZD4522 | 10 |
| Povidone | 10 |
| Mannitol | 187.6 |
| Microcrystalline cellulose | 188.0 |
| Tribasic calcium phosphate | 80.0 |
| Sodium starch glycollate | 12.0 |
| Butylated hydroxytoluene | 0.2 |
| Magnesium stearate | 6.0 |

EXAMPLE 3

| | |
|---|---|
| ZD4522 | 20 |
| Povidone | 3.73 |
| Mannitol | 69.41 |
| Microcrystalline cellulose | 70.21 |
| Tribasic calcium phosphate | 29.88 |
| Sodium starch glycollate | 4.48 |
| Butylated hydroxytoluene | 0.05 |
| Magnesium stearate | 2.0 |

Tablets containing 40 mg of the ZD4522 can be obtained by doubling the quantities given in Example 3.

What is claimed is:

1. A method for treating heterozygous familial hypercholesterolemia in a patient suffering heterozygous familial hypercholesterolemia, comprising administering to the patient (E)-7-[4-(4-fluorophenyl)-6-isopropyl-2-[methyl(methylsulfonyl)amino]pyrimidin-5-yl](3R,5S)-3,5-dihydroxyhept-6-enoic acid or a pharmaceutically acceptable salt thereof.

2. A method as claimed in claim 1 wherein the patient is suffering from severe heterozygous familial hypercholesterolemia.

3. A method as claimed in claim 1 wherein the patient also suffers one or more of the following conditions coronary heart disease, peripheral vascular disease and diabetes.

4. A method as claimed in claim 1 or claim 3 wherein the target LDL-C level for the patient suffering heterozygous familial hypercholesterolemia which is to be achieved by administering to the patient (E)-7-[4-(4-fluorophenyl)-6-isopropyl-2-[methyl(methylsulfonyl)amino]pyrimidin-5-yl](3R,5S)-3,5-dihydroxyhept-6-enoic acid or a pharmaceutically acceptable salt thereof is less than or equal to $\leq 100$ mg/dL.

5. A method as claimed in claim 4 wherein the calcium salt of (E)-7-[4-(4-fluorophenyl)-6-isopropyl-2-[methyl(methylsulfonyl)amino]pyrimidin-5-yl](3R,5S)-3,5-dihydroxyhept-6-enoic acid is administered.

6. A method as claimed in claim 5 wherein 40 to 80 mg of (E)-7-[4-(4-fluorophenyl)-6-isopropyl-2-[methyl(methylsulfonyl)amino]pyrimidin-5-yl](3R,5 S)-3,5-dihydroxyhept-6-enoic acid is administered once a day to the patient in the form of the calcium salt.

7. A method as claimed in claim 5 wherein 80 mg of (E)-7-[4-(4-fluorophenyl)-6-isopropyl-2-[methyl(methylsulfonyl)amino]pyrimidin-5-yl](3R,5S)3,5-dihydroxyhept-6-enoic acid is administered once a day to the patient in the form of the calcium salt.

8. A method for reducing LDL-C, raising HDL-C, reducing Apo B and raising Apo A-I in a patient suffering from heterozygous familial hypercholesterolemia comprising administering to the subject (E)-7-[4-(4-fluorophenyl)-6-isopropyl-2-[methyl(methylsulfonyl)amino]pyrimidin-5-yl](3R,5S)-3,5-dihydroxyhept-6-enoic acid or a pharmaceutically acceptable salt thereof.

9. A method as claimed in claim 1 wherein the patient has a fasting LDL-C level between 5.69 and <12.93 mmol/L.

10. A method as claimed in claim 9 wherein the patient has a fasting triglyceride level less than or equal to 4.52 mmol/L.

* * * * *